United States Patent

Kimura et al.

[11] Patent Number: 6,133,327
[45] Date of Patent: Oct. 17, 2000

[54] AEROSOL PREPARATION

[75] Inventors: Fuminori Kimura; Tsuyoshi Uchiyama; Haruo Shimamura; Fumio Urushizaki, all of Tokyo, Japan

[73] Assignee: Taisho Pharmaceutical Co., Ltd., Japan

[21] Appl. No.: 09/091,101

[22] PCT Filed: Dec. 12, 1996

[86] PCT No.: PCT/JP96/03631

§ 371 Date: Jun. 12, 1998

§ 102(e) Date: Jun. 12, 1998

[87] PCT Pub. No.: WO97/21426

PCT Pub. Date: Jun. 19, 1997

[30] Foreign Application Priority Data

Dec. 14, 1995 [JP] Japan .................................. 7-325335

[51] Int. Cl.$^7$ .................................. C09K 3/30; A61K 9/12
[52] U.S. Cl. .................................. 516/8; 424/45; 514/817; 514/830; 514/944
[58] Field of Search .................................. 516/8; 424/45; 514/817, 830, 944

[56] References Cited

U.S. PATENT DOCUMENTS

| | | | |
|---|---|---|---|
| 3,584,115 | 6/1971 | Gebhart et al. | 424/45 |
| 4,495,169 | 1/1985 | Schmolka | 424/45 X |
| 4,588,581 | 5/1986 | Schmolka | 424/45 |
| 4,981,678 | 1/1991 | Tomlinson | 424/45 |
| 5,143,717 | 9/1992 | Davis | 424/45 |
| 5,209,921 | 5/1993 | Brobyn et al. | 424/45 |
| 5,352,437 | 10/1994 | Nakagawa et al. | 424/45 |
| 5,397,564 | 3/1995 | Seki et al. | 424/45 |
| 5,527,832 | 6/1996 | Chi et al. | 514/944 X |

FOREIGN PATENT DOCUMENTS

| | | | |
|---|---|---|---|
| 409555 | 9/1966 | Australia | 424/45 |
| 2255890 | 10/1990 | Japan . | |
| 4103526 | 4/1992 | Japan . | |
| 2137090A | 10/1984 | United Kingdom . | |
| 9011068 | 4/1990 | WIPO . | |

*Primary Examiner*—Richard D. Lovering
*Attorney, Agent, or Firm*—Lorusso & Loud

[57] ABSTRACT

An aerosol preparation which when sprayed forms a sherbet-like solid, which comprises a concentrate containing a lower alcohol having 1 to 3 carbon atoms and a higher alcohol having at least 12 carbon atoms and a propellant containing a liquefied gas. Said aerosol preparation does not require any complicated emulsifying procedure for the production, can contain components labile in water and have a durable cooling effect, and therefore, it is quickly calmative on the pain caused by contusion, sprain, muscular fatigue, etc. and the itch caused by athlete's foot, insect bite, etc.

5 Claims, No Drawings

AEROSOL PREPARATION

This application is a 371 of PCT/JP96/03631 filed Dec. 12, 1996.

TECHNICAL FIELD

The present invention relates to an aerosol preparation which when sprayed forms a sherbet-like solid on the sprayed site and has an enhanced cooling effect.

BACKGROUND ART

It is effective to cool the affected part in order to quickly calm the pain caused by contusion, sprain, muscular fatigue, etc. or the itch caused by athlete's foot, insect bite, etc. In the past, the aerosol preparations which when sprayed do not form a sherbet-like solid have been used frequently for such symptoms. However, since such aerosol preparations do not have a durable cooling effect on the skin, a durable calming effect of pain or itch on the affected part cannot be achieved by these aerosol preparations. The specifications of WO90/11068 and Japanese Patent Kokai 4-103526 disclose aerosol preparations which form a sherbet-like foam gel for solving such drawbacks. However, such prior art aerosol preparations require complicated procedures such as heating and emulsifying procedures for the production of the concentrate, and have a problem of low efficacy in the production.

In addition, it is essential to contain water in the known aerosol preparations which when sprayed form a sherbet-like solid, because the durable cooling effect of these preparations can be obtained by freezing water which is contained therein. Accordingly, it is impossible to contain drugs labile in water or highly lipophilic drugs in the known preparations.

DISCLOSURE OF THE INVENTION

As a result of extensive research in order to solve the above-mentioned purposes, the present inventors have found that an aerosol preparation comprising a lower alcohol, a higher alcohol and a liquefied gas does not require an emulsifying procedure for the production and has a durable cooling effect because the aerosol preparation forms a sherbet-like solid when sprayed, and whereby the present invention has been accomplished.

That is, the present invention relates to an aerosol preparation which when sprayed forms a sherbet-like solid, which comprises a concentrate containing a lower alcohol having 1 to 3 carbon atoms and a higher alcohol having at least 12 carbon atoms, and a propellant containing a liquefied gas.

Any known aerosol preparations form a solid, when sprayed, by freezing water which is contained therein, on the contrary, the aerosol preparation of the present invention does not always necessarily contain water, and it is characterized by that the aerosol preparation forms a solid under entirely new conditions when sprayed.

According to the aerosol preparation of the present invention, the higher alcohol which is cooled by the heat of vaporization of the liquefied gas including the lower alcohol forms a sherbet-like solid when sprayed.

In the present invention, the lower alcohol having 1 to 3 carbon atoms means a straight or branched alcohol, for example, methanol, ethanol, denatured ethanol, propanol, isopropanol, etc., and preferably ethanol. The amount of the lower alcohol is preferably 0.3 to 65% by weight based on the total amount of the preparation, more preferably 1.5 to 50% by weight and most preferably 15 to 35% by weight. If the amount of the lower alcohol is less than 0.3% by weight, the concentrate cannot be easily mixed with the propellant homogeneously. If the amount of the lower alcohol is more than 65% by weight, since the amount of the propellant is relatively reduced, the cold feeling is reduced.

The higher alcohol having at least 12 carbon atoms of the present invention means a straight or branched alcohol which can be homogeneously mixed with other components, for example, lauryl alcohol, cetanol, stearyl alcohol, cetostearyl alcohol, behenyl alcohol, lanolin alcohol, hydrogenated lanolin alcohol, etc, they may be used alone or by mixture with each other, and stearyl alcohol or cetanol is preferable.

The amount of the higher alcohol is preferably 0.005 to 14% by weight based on the total amount of the preparation, more preferably 0.015 to 10% by weight and most preferably 0.5 to 5% by weight. If the amount of the higher alcohol is less than 0.005% by weight, since the aerosol preparation cannot easily form the solid when sprayed, the durable cold feeling is reduced. On the other hand, if the amount of the higher alcohol is more than 14% by weight, since the higher alcohol cannot be easily dissolved, the production procedure is complicated.

The higher alcohol must be absolutely dissolved in the lower alcohol and the liquefied gas so as to give a homogeneous system, and whereby the effect of the present invention can be achieved. For the purpose, when the higher alcohol cannot be sufficiently dissolved, it is possible to contain other solvents or solubilizing agents (e.g. polyoxyethylene alkyl ether, polyoxyethylene hydrogenated castor oil, diisopropyl adipate, isopropyl myristate, 1,3-butyleneglycol, propyleneglycol, polyethyleneglycol, glycerin, lactic acid, sodium hydroxide, etc.).

The liquefied gas is any one which can be used as a propellant for an ordinary aerosol preparation, but preferably dimethyl ether, n-butane, i-butane, propane or a liquefied petroleum gas, and they can be used alone or by mixture with each other. The amount of the liquefied gas is preferably 30 to 95% by weight based on the total amount of the preparation, and more preferably 50 to 85% by weight. If the amount of the liquefied gas is less than 30% by weight, the cold feeling by the aerosol preparation is reduced, and whereby the calming effect of pain and itch is reduced. On the other hand, if the amount of the liquefied gas is more than 95% by weight, the aerosol preparation does not form a sherbet-like solid when sprayed, and therefore the durable cooling effect cannot be easily obtained.

When the conditions for which the aerosol preparation of the present invention forms a sherbet-like solid are distinguished between the concentrate and the propellant of the aerosol preparation, it is necessary to contain at least 6% by weight of the lower alcohol having 1 to 3 carbon atoms in the concentrate, at least 1% by weight of the higher alcohol having at least 12 carbon atoms in the concentrate and 0.5 to 20 parts by weight of the liquefied gas based on 1 part by weight of the concentrate.

The aerosol preparation of the present invention can be prepared by dissolving the lower alcohol and the higher alcohol to give a homogeneous system, and if desired, adding such other components that do not destroy the homogeneous system, and filling the resulting concentrate together with the liquefied gas into an aerosol container. Examples of the aerosol container include containers made of metals or plastics as used usually. In view of the durable cooling effect, it is preferable to contain a suitable amount of water as such another component that does not destroy the homogeneous system. In case of addition of water to the concentrate, not more than 90% by weight of water can be added based on the total amount of the concentrate, but preferably 20 to 60% by weight of water is added to the concentrate in view of easy preparation design.

In order to enhance the calming effect on pain and itch on the affected part, the aerosol preparation of the present invention can contain such drug-effective ingredients that do not degrade the effect of the present invention, for example, anti-inflammatory and analgesic agents (e.g. indomethacin, methyl salicylate, monoglycol salicylate, ketoprofen, flurbiprofen, piroxicam, diclofenac, ibuprofen, mephenamic acid, dexamethasone acetate, etc.), antipruritics (e.g. crotamiton, ichthammol, mochthamol, thymol acid, etc.), antifungal agents (e.g. amorolfin hydrochloride, undecylenic acid, pentachlorophenol, clotrimazole, tolnaftate, trichomycin, miconazole nitrate, lanoconazole, sulconazole nitrate, oxyconazole nitrate, bifonazole, etc.), antihistaminic agents (e.g. diphenhydramine, diphenhydramine hydrochloride, isothipendyl hydrochloride, etc.), local anesthetics (e.g. lidocaine, dibucaine hydrochloride, etc.), antibiotics (e.g. potassium iodide, chlorohexidine gluconate, acrinol, benzalkonium chloride, etc.), antiphlogistics (e.g. penicillin, tetracycline hydrochloride, fradiomycin, kanamycin, etc.), refrigerants (e.g. 1-menthol, camphor, mentha oil, etc.), and the like. The amounts of these drug-effective components are different individually, but preferably 0.001 to 10% by weight based on the total amount of the preparation.

The aerosol preparation of the present invention can contain, if necessary, any additives usable for ordinary aerosol preparations as long as they do not degrade the effect of the present invention, for example, anti-oxidants (e.g. dibutylhydroxytoluene, etc.), percutaneous absorption promoters (e.g. glycerin esters of fatty acid, fats, aliphatic carboxylates, nicotinates, azone, alkyleneglycol esters of fatty acid, etc.), perfumes, dyes and the like.

INDUSTRIAL UTILIZABILITY

The present invention makes it possible to provide an aerosol preparation which when sprayed forms a sherbet-like solid, does not require a complicated emulsifying procedure for the production, and has a cooling effect comparable to that of the prior art products.

BEST MODE FOR CARRYING OUT THE INVENTION

The present invention is illustrated in more detail by the following examples and test example.

EXAMPLE 1

4.76 parts by weight of stearyl alcohol and 28.53 parts by weight of ethanol were mixed, stirred and dissolved homogeneously to give a concentrate. The concentrate was filled into a pressure-resistant container, and a valve was attached to the container, into which 0.07 part by weight of propane, 1.93 parts by weight of n-butane, 0.93 part by weight of i-butane and 63.78 parts by weight of dimethyl ether were then filled. A spout for spraying was attached to the container to give an aerosol preparation.

EXAMPLE 2

0.31 part by weight of indomethacin, 4.11 parts by weight of diisopropyl adipate, 1.23 parts by weight of polyoxyethylene alkyl ether, 16.47 parts by weight of denatured ethanol, 13.39 parts by weight of purified water and 1.23 parts by weight of cetanol were mixed, stirred and dissolved homogeneously to give a concentrate. The concentrate was filled into a pressure-resistant container, and a valve was attached to the container, into which 63.26 parts by weight of dimethyl ether was then filled. A spout for spraying was attached to the container to give an aerosol preparation.

EXAMPLE 3

0.35 part by weight of miconazole nitrate, 1.76 parts by weight of diisopropyl adipate, 1.05 parts by weight of isopropyl myristate, 0.70 part by weight of glycerin, 15.80 parts by weight of denatured ethanol and 8.74 parts by weight of purified water, 0.53 part by weight of stearyl alcohol, 0.53 part by weight of cetanol, 0.70 part by weight of polyoxyethylene alkyl ether and 0.35 part by weight of polyoxyethylene hydrogenated castor oil were mixed, stirred and dissolved homogeneously to give a concentrate. The concentrate was filled into a pressure-resistant container, and a valve was attached to the container, into which 69.49 parts by weight of dimethyl ether was then filled. A spout for spraying was attached to the container to give an aerosol preparation.

Comparative Example 1

Following the same method as in Example 1 using the formulation of Example 1 in which stearyl alcohol was replaced with ethanol, there was obtained an aerosol preparation.

Comparative Example 2

Following the same method as in Example 2 using the formulation of Example 2 in which polyoxyethylene alkyl ether and cetanol were replaced with denatured ethanol and purified water respectively, there was obtained an aerosol preparation for comparison.

Comparative Example 3

0.36 part by weight of miconazole nitrate, 1.79 parts by weight of diisopropyl adipate, 1.07 parts by weight of isopropyl myristate, 0.71 part by weight of glycerin, 17.06 parts by weight of denatured ethanol and 8.27 parts by weight of purified water were mixed, stirred and dissolved homogeneously to give a concentrate. The concentrate was filled into a pressure-resistant container, and a valve was attached to the container, into which 70.74 parts by weight of dimethyl ether was then filled. A spout for spraying was attached to the container to give an aerosol preparation for comparison.

Comparative Example 4

(An aerosol preparation which requires an emulsifying procedure for the production)

0.31 part by weight of indomethacin, 4.07 parts by weight of diisopropyl adipate, 1.22 parts by weight of polyoxyethylene sorbitan monostearate, 0.81 part by weight of polyoxyethylene sorbitan tristearate and 1.22 parts by weight of sorbitan monostearate were dissolved with heating, and mixed thoroughly with 15.94 parts by weight of hot purified water. After cooling with stirring, the mixture was mixed with 14.23 parts by weight of denatured ethanol and dispersed homogeneously to give a concentrate. The concentrate was filled into a pressure-resistant container, and a valve was attached to the container, into which 62.20 parts by weight of dimethyl ether was then filled. A spout for spraying was attached to the container to give an aerosol preparation.

Test Example 1

A thermocouple sensor was fixed on a piece of sheet with adhesive tapes, and the sheet was spread on a thermostat water bath controlled at 33° C. The aerosol preparations obtained in Examples 1 to 3 and Comparative Examples 1 to 4 were each sprayed on the thermocouple sensor for 3 seconds. Properties of the aerosol preparation were confirmed when sprayed, and the values shown by the thermocouple sensor with time were measured. Results are shown in Table 1.

TABLE

| Sample | Emulsifying procedure | Sherbet | Change of the temperature of thermocouple sensor (° C.) | | | | | | | |
|---|---|---|---|---|---|---|---|---|---|---|
| | | | before spray | 15 sec. | 30 sec. | 45 sec. | 60 sec. | 90 sec. | 120 sec. | 180 sec. |
| Example 1 | unnecessary | form | 33.5 | 18.4 | 20.8 | 21.5 | 23.5 | 24.6 | 30.7 | 33.0 |
| Example 2 | unnecessary | form | 33.5 | 14.8 | 15.3 | 18.8 | 23.5 | 26.1 | 29.3 | 31.5 |
| Example 3 | unnecessary | form | 33.2 | 15.0 | 14.7 | 15.6 | 20.2 | 22.9 | 31.6 | 32.9 |
| Comparative Example 1 | unnecessary | no form | 33.3 | 30.9 | 31.9 | 32.0 | 32.4 | 32.6 | 33.2 | 33.2 |
| Comparative Example 2 | unnecessary | no form | 33.3 | 23.0 | 30.5 | 32.5 | 32.9 | 33.0 | 33.3 | 33.2 |
| Comparative Example 3 | unnecessary | no form | 33.4 | 22.0 | 31.9 | 32.1 | 32.4 | 32.9 | 33.0 | 33.3 |
| Comparative Example 4 | necessary | form | 33.3 | 15.8 | 15.5 | 18.9 | 23.0 | 31.2 | 31.2 | 33.0 |

The aerosol preparations of Examples 1 to 3 and Comparative Example 4 formed a sherbet-like solid when sprayed, but those of Comparative Examples 1 to 3 did not form any sherbet-like solid. In the change of temperature on the thermocouple sensor, the temperatures by the aerosol preparations of Comparative Examples 1 to 3 were at least 30° C. at 30 seconds after the spray and returned to the original temperature at 45 seconds after the spray, on the contrary, the aerosol preparations of Examples 1 to 3 and Comparative Example 4 were found to have a durable cooling effect.

What is claimed is:

1. An aerosol preparation which when sprayed forms a sherbet-like solid, which comprises:

(A) a concentrate containing:
0.3 to 65% by weight, based on the total amount of the preparation, of a lower alcohol having 1 to 3 carbon atoms; and
0.005 to 14% by weight, based on the total amount of the preparation, of a higher alcohol having at least 12 carbon atoms, and (B) a propellant containing 50 to 85% by weight, based on the total amount of the preparation, of dimethyl ether.

2. The aerosol preparation according to claim 1 wherein the lower alcohol having 1 to 3 carbon atoms is in an amount of at least 6% by weight based on the concentrate, the higher alcohol having at least 12 carbon atoms is in an amount of at least 1% by weight based on the concentrate, and the liquefied gas is in an amount of 0.5 to 20 parts by weight based on 1 part by weight of the concentrate.

3. The aerosol preparation according to claim 1 wherein the lower alcohol is ethanol.

4. The aerosol preparation according to claim 1 wherein the higher alcohol is at least one alcohol selected from the group consisting of stearyl alcohol and cetanol.

5. The aerosol preparation according to claim 1 wherein the concentrate contains 20 to 60% by weight of water.

* * * * *